(12) United States Patent
McNair

(10) Patent No.: US 11,544,603 B1
(45) Date of Patent: Jan. 3, 2023

(54) DECISION SUPPORT TOOL FOR MITIGATING EMERGENCY DEPARTMENT (ED) CONGESTION

(71) Applicant: CERNER INNOVATION, INC., Kansas City, KS (US)

(72) Inventor: Douglas S. McNair, Leawood, KS (US)

(73) Assignee: CERNER INNOVATION, INC., North Kansas City, MO (US)

( * ) Notice: Subject to any disclaimer, the term of this patent is extended or adjusted under 35 U.S.C. 154(b) by 1356 days.

(21) Appl. No.: 15/858,443

(22) Filed: Dec. 29, 2017

Related U.S. Application Data

(60) Provisional application No. 62/441,058, filed on Dec. 30, 2016.

(51) Int. Cl.
| | | |
|---|---|---|
| *G16H 50/20* | (2018.01) | |
| *G16H 50/50* | (2018.01) | |
| *A61B 5/00* | (2006.01) | |
| *G06N 5/04* | (2006.01) | |
| *G06Q 10/04* | (2012.01) | |
| *G16H 10/60* | (2018.01) | |

(52) U.S. Cl.
CPC .............. *G06N 5/045* (2013.01); *G06Q 10/04* (2013.01); *G16H 10/60* (2018.01)

(58) Field of Classification Search
CPC ......... G06N 5/045; G06Q 10/04; G16H 10/60
USPC ...................................................... 706/1–62
See application file for complete search history.

(56) References Cited

U.S. PATENT DOCUMENTS

| | | | |
|---|---|---|---|
| 6,144,877 A | 11/2000 | DePetrillo | |
| 6,438,419 B1* | 8/2002 | Callaway | A61N 1/3925 600/508 |
| 8,515,777 B1* | 8/2013 | Rajasenan | G16H 40/20 705/2 |
| 9,311,449 B2 | 4/2016 | Levin et al. | |
| 2004/0243328 A1* | 12/2004 | Rapp | A61B 5/4094 702/71 |
| 2005/0197544 A1 | 9/2005 | Bernstein | |
| 2011/0306846 A1* | 12/2011 | Osorio | G16H 40/67 600/301 |

(Continued)

OTHER PUBLICATIONS

U.S. Appl. No. 15/392,715, filed Dec. 28, 2016, titled "Healthcare Resource Scheduling", inventor Douglas S. McNair.

*Primary Examiner* — Brandon S Cole
(74) *Attorney, Agent, or Firm* — Shook, Hardy and Bacon L.L.P.

(57) ABSTRACT

A technology is provided for predicting congestion or crowding of services over a future time interval, and may be utilized for forecasting congestion in a hospital emergency department. One embodiment of this technology comprises a decision support tool for resources management to prevent overcrowding and long waiting times, or for mitigating ED congestion by, for example, warning hospital managers that a significant likelihood exists of ED congestion over a future time frame, or automatically initiating mitigative actions. A time series of consecutive ED arrivals timestamps is processed to determine a presence (or absence) of positive autocorrelation or self-similarity and estimate Hurst exponent values to generate a forecast model. The forecast model is utilized to determine future ED demand.

18 Claims, 11 Drawing Sheets

(56) References Cited

U.S. PATENT DOCUMENTS

| | | | |
|---|---|---|---|
| 2014/0136458 A1* | 5/2014 | Levin | G16H 50/20 |
| | | | 706/21 |
| 2014/0297302 A1 | 10/2014 | Vanier et al. | |
| 2015/0242577 A1* | 8/2015 | Konoske | G16H 50/50 |
| | | | 705/2 |
| 2017/0251985 A1* | 9/2017 | Howard | A61B 5/165 |
| 2017/0359261 A1* | 12/2017 | Avci | H04L 47/127 |

* cited by examiner

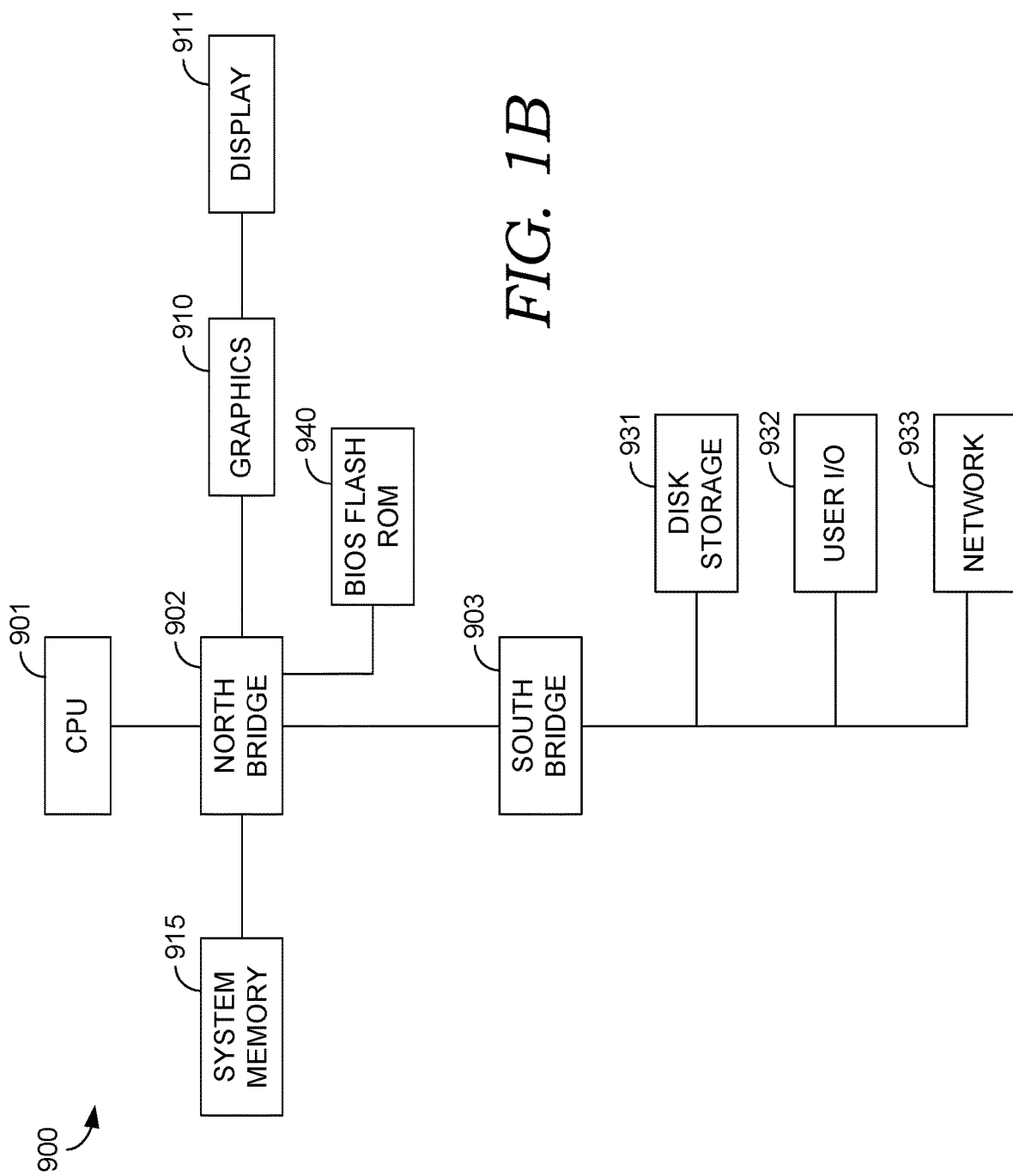

300

EXAMPLE - PATTERNS IN ED ARRIVALS TIME SERIES

| enc_typ | wk | id | dt-tm |
|---|---|---|---|
| EMERGENCY | 1 | 2680401 | 2/1/2016 0:03 |
| EMERGENCY | 1 | 2680404 | 2/1/2016 0:04 |
| EMERGENCY | 1 | 2680407 | 2/1/2016 0:08 |
| EMERGENCY | 1 | 2680410 | 2/1/2016 0:10 |
| EMERGENCY | 1 | 2680416 | 2/1/2016 0:20 |
| EMERGENCY | 1 | 2680419 | 2/1/2016 0:22 |
| EMERGENCY | 1 | 2680422 | 2/1/2016 0:25 |
| EMERGENCY | 1 | 2680425 | 2/1/2016 0:29 |
| EMERGENCY | 1 | 2680428 | 2/1/2016 0:33 |
| EMERGENCY | 1 | 2680431 | 2/1/2016 0:38 |
| EMERGENCY | 1 | 2680437 | 2/1/2016 0:48 |
| EMERGENCY | 1 | 2680440 | 2/1/2016 0:49 |
| EMERGENCY | 1 | 2680443 | 2/1/2016 0:51 |
| EMERGENCY | 1 | 2680446 | 2/1/2016 0:58 |
| EMERGENCY | 1 | 2680449 | 2/1/2016 0:58 |
| EMERGENCY | 1 | 2680452 | 2/1/2016 1:02 |
| EMERGENCY | 1 | 2680455 | 2/1/2016 1:05 |
| EMERGENCY | 1 | 2680464 | 2/1/2016 1:15 |
| EMERGENCY | 1 | 2680458 | 2/1/2016 1:16 |
| EMERGENCY | 1 | 2680461 | 2/1/2016 1:18 |

DESCRIPTIVE STATISTICS OF H DISTRIBUTION, FOR EXAMPLE
DATA SET OF 68,914 ED ARRIVALS, 18 WEEKS

| PERCENTILE | HURST EXPONENT |
|---|---|
| 5 | 0.49 |
| 10 | 0.56 |
| 25 | 0.60 |
| 50 | 0.62 |
| 75 | 0.64 |
| 90 | 0.67 |
| 95 | 0.70 |
| 99 | 0.81 |

*FIG. 5B.*

STATISTICAL PERFORMANCE FOR PREDICTING COMPOSITE OUTCOME
OF ED DIVERSION OR SERVICE TIME EXCEEDING 75TH PERCENTILE 15
MIN AHEAD, FROM EWMA-SMOOTHED ARIMA FORECAST OF H

| PROPERTY | VALUE (95% CI) |
|---|---|
| SENSITIVITY | 95% (92% TO 98%) |
| SPECIFICITY | 89% (84% TO 94%) |
| POSITIVE PREDICTIVE VALUE | 84% (78% TO 90%) |
| NEGATIVE PREDICTIVE VALUE | 97% (94% TO 99%) |
| PREVALENCE | 37% (29% TO 45%) |

*FIG. 5C.*

```
#########################################################################

#  Hurst exponent model of ED congestion/diversion

################################################################### library(timeDate)
library(lubridate)
library(dplyr)
library(magrittr)
library(zoo)
library(pracma)
library(qcc)
library(forecast)

# inits
vislen <- length(vis[,1])
hurst_ts <- rep(0, vislen)
hurst_ts2 <- rep(0, vislen)
hurst_ucl_ahead <- rep(0, vislen)
conf <- 75
N <- 3
epoch <- 5
M1 <- 240
M2 <- 12
M3 <- 25 load arrivals time series event data
vis <- read.csv(file="c:/0_cerdsm/IP/ED_queueing_flow/NmbVisitsDataSet.csv", header=TRUE,
        strip.white=TRUE, colClasses=c("factor","integer",rep("character",2)), allowEscapes=TRUE, skipNul=TRUE)
vis$dt_tm <- as.POSIXct(vis$dt_tm, format="%m/%d/%Y %H:%M", tz="EST5EDT", usetz=FALSE)
```

.
.
.

CONTINUES IN FIG. 6B

*FIG. 6A.*

CONTINUES FROM FIG. 6A

```
# determine ensemble-model estimates Hurst exponent time series of recent epochs
for (i in 1:(vislen - M1)) {
    df1 <- data.frame(off=sort(as.numeric(vis$dt_tm[i:(i+M1)])/60, decreasing=TRUE))  # most recent 240-sample window of offsets in minutes
    df2 <- data.frame(off=df1$off[1:min(which(df1$off < df1$off[1] - 119))])          # only retain most recent 120 min exclusive
    df2$off <- df2$off - min(df2$off)                                                  # indexed from zero
    df2$ep <- as.integer(df2$off %/% epoch)                                            # rolling 5-min epochs, 288 per 24 hours
    nbr <- df2 %>% count(ep)                                                           # count nbr visits arriving per 5 min epoch
    nbr <- nbr[,2]                                                                     # extract just the counts
    ts <- as.ts(nbr, freq=1)                                                           # cast counts as time series data type
    s <- sd(ts)                                                                        # check to see if counts are identical, since Hurst exp estimation
    #                                                                                     fails for constant time series
    if (s == 0) ts[1] <- ts[1] + 1                                                     # if identical then increment first epoch by 1
    hurst2 <- hurstexp(ts, d=20, display=FALSE)                                        # plurality of estimates of Hurst exponent by different methods
    hurst_ts[i] <- max(0, min(1, mean(hurst2$Hal, hurst2$Hs)))                         # ensemble mean of empirical and R/S estimations of Hurst
    #                                                                                     exponent, constrained to [0,1] range
} apply exponentially-weighted moving average (EWMA) smoothing to ensemble model Hurst exponent time series
M2m1 <- M2 - 1
for (i in 1:(vislen - M2m1)) {
    hurst_ts2[i + M2m1] <- ewmaSmooth(1:M2, hurst_ts[i:(i + M2m1)], lambda=0.2)$y[M2]
} determine ARIMA model 75th percentile forecast for period beyond current time
M3m1 <- M3 - 1
for (i in 2:(vislen - M3)) {
    fit <- Arima(as.ts(hurst_ts2[i:(i + M3m1)]), order=c(3,1,0))
    fore <- try(forecast(fit, h=N, level=conf)$upper[N])
    if(is.number(fore)) {
        hurst_ucl_ahead[i] <- fore
    } else {
        hurst_ucl_ahead[i] <- hurst_ucl_ahead[i-1]
    }
} emit alarm when 15 min (3*5-min epochs) from now the 75th percentile of Hurst exponent is predicted to be > 0.80
```

FIG. 6B

DECISION SUPPORT TOOL FOR MITIGATING EMERGENCY DEPARTMENT (ED) CONGESTION

CROSS-REFERENCE TO RELATED APPLICATIONS

This application claims the benefit of U.S. Provisional Application No. 62/441,058; entitled "DECISION SUPPORT TOOL FOR MITIGATING EMERGENCY DEPARTMENT (ED) CONGESTION," filed Dec. 30, 2016, which is expressly incorporated by reference in its entirety.

BACKGROUND

Hospital emergency department (ED) congestion has been identified as a major public health problem in the United States. ED congestion is associated with adverse patient outcomes and contributes to lost services revenue when patients leave without being seen and when hospital-based EDs go on-diversion. An ED that is experiencing congestion and delays that has become unacceptably large is placed "on-diversion" for redirection of persons requiring emergency medical care. The "on-diversion" status persists until the congestion condition has abated sufficiently, at which time arrivals are once again accepted to the ED.

Common causes of crowding include high rates of non-urgent visits, visits by high-utilizer ("frequent-flyer") patients, seasonal influenza and other viral illness outbreaks, inadequate staffing, ED boarding of patients awaiting inpatient beds, and hospital bed shortages, for administrative reasons and for reasons of prolonged lengths of stay. Common approaches to managing and mitigating crowding include adding personnel, opening observation units, restricting non-urgent referrals, placing physicians in a triage role, introducing an attending-physician "float shift," smoothing elective surgery caseloads, and instituting ambulance diversion control. In some instances, ED crowding affords a net financial benefit to some hospitals. This is because ED crowding and ED "on-diversion" status allow the hospitals to maximize inpatient bed occupancy by well-insured, elective patients while patients without commercial insurance are "boarded" in the ED or are diverted to other institutions or elope without being seen.

But the consequences of ED crowding are prevalent and adversely affect public health. These consequences may include delayed treatment, medication errors and other errors in patient treatment, patient elopement without being examined or treated, possible increased rate of readmissions to hospital, increased mortality, low patient/family satisfaction, inferior Press Ganey quality scores, and financial losses. Thus, prediction and prevention of ED crowding appear to be more efficacious than the present conventional approaches to managing ED crowding once it has materialized. While there have been attempts to provide a technological solution to mitigate ED crowding through decision support systems, these systems have significant drawbacks and cannot provide the reliability and accuracy of the systems and processes proposed in the present disclosure.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

Technologies are provided for automatically detecting a probability of ED crowding occurring over a future time interval and for forecasting ED congestion. A decision support tool is provided for resources management to prevent overcrowding and long waiting times, and in some embodiments for mitigating ED congestion by, for example, warning hospital managers that a significant likelihood exists of ED congestion over a future time frame, and automatically initiating (or recommending, or facilitating initiation of) mitigative actions to enhance throughput and prevent congestion, crowding, or excessive waiting times in services queues of hospital emergency departments. In particular, embodiments described herein analyze a time series of consecutive ED arrivals timestamps to determine a presence (or absence) of positive autocorrelation or self-similarity and estimate Hurst exponent values to generate a forecast model (e.g., for forecasting near-term future Hurst exponent values) that can be utilized to predict future ED demand. In this way, embodiments of the present disclosure enable reliable forecasting of near-term congestion so as to enable managers of the service to undertake appropriate actions as may prevent the congestion, diminish its severity or duration, or reduce average services congestion over time. Further, in some instances, the forecast may be provided to ED patients waiting to be seen or potential patients en route to an ED, thereby having an effect of improving satisfaction for persons waiting in such queues when accurate forecast information is provisioned to them and enabling additional efforts to be made by ED staff to enhance their comfort during waiting.

Further still, some embodiments of the decision support tool may be utilized for load-balancing across a pool of service-providing resources such as multiple hospital emergency departments in a city or region. For instance, where it is determined that an ED resource has low recent Hurst exponent values and forecast Hurst exponent values may reasonably accept a larger share of the incident arrivals from elsewhere (for example, accepting transport of patients who have been diverted from other emergency departments) without incurring notable increases in their Hurst exponent and queueing self-similarity or service times, thus accomplishing safe and effective load-balancing. Some embodiments further automatically initiate load-balancing actions (such as rerouting patients en-route to EDs, scheduling resources, or issuing electronic notifications to potential patients, caregivers, or EDs).

BRIEF DESCRIPTION OF THE DRAWINGS

The present technology is described in detail below with reference to the attached drawing figures, wherein:

FIGS. 1A and 1B depict aspects of an illustrative operating environment suitable for practicing an embodiment of the present disclosure;

FIG. 3 depicts an example time series for ED arrivals, suitable for use by an embodiment of the present disclosure;

Figure 4A:
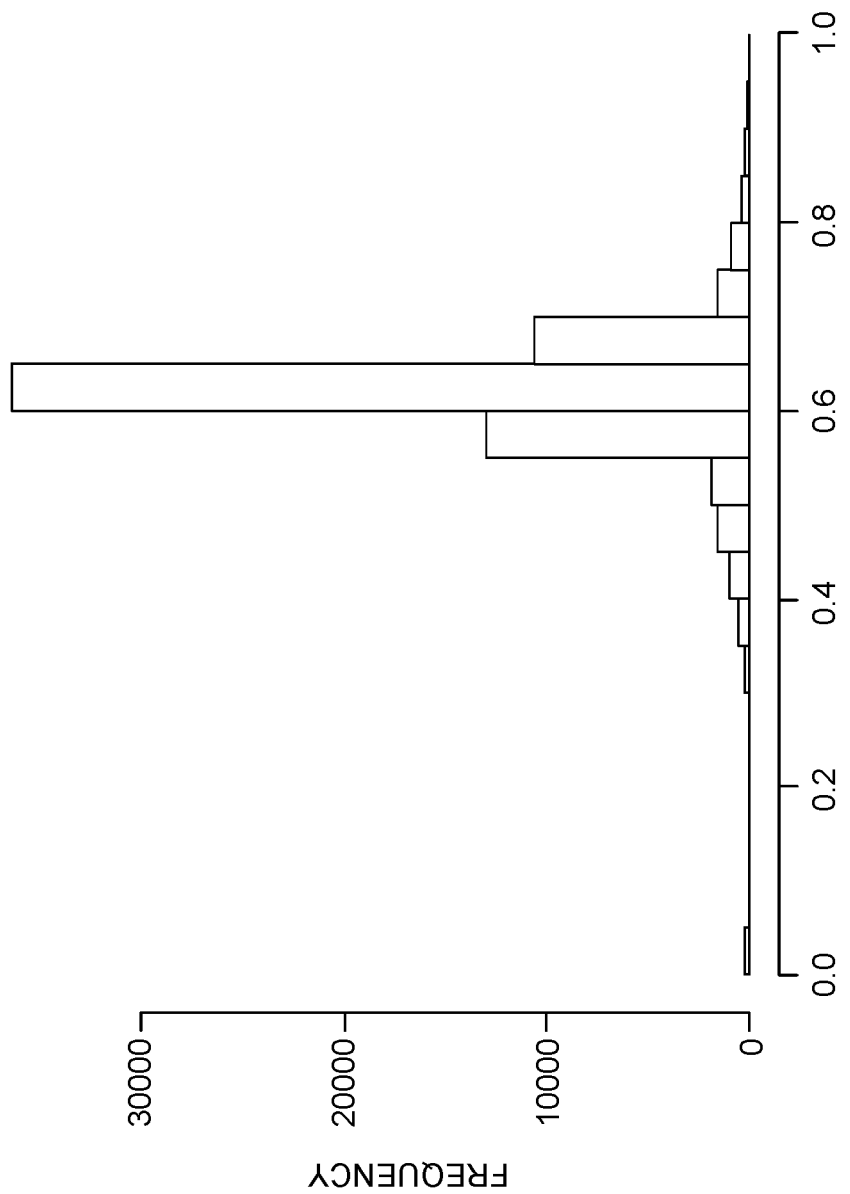
FIG. 4A depicts an example of the $75^{th}$-percentile Hurst exponent distributions for a 15-minute future interval from an autoregressive integrated moving average (ARIMA)
Figure 4B:
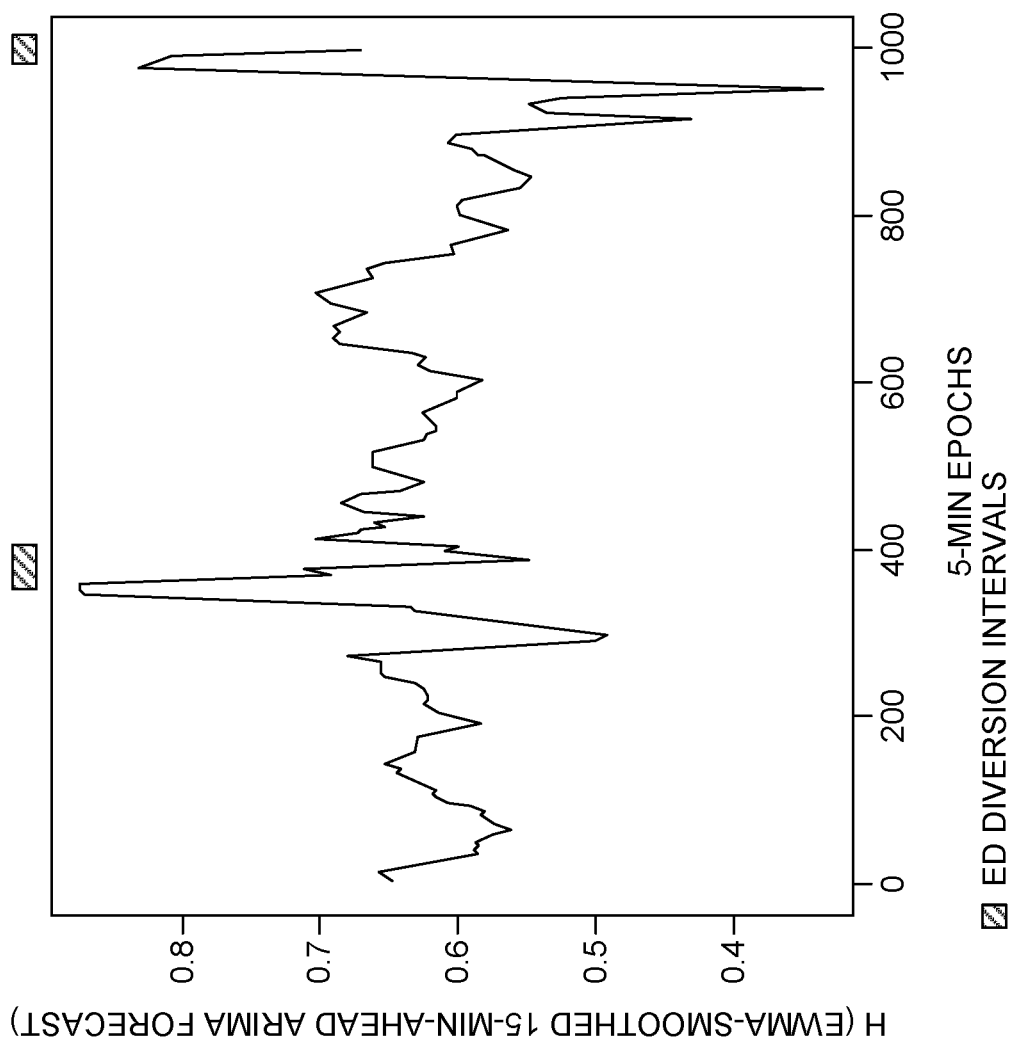
Figure 5A:
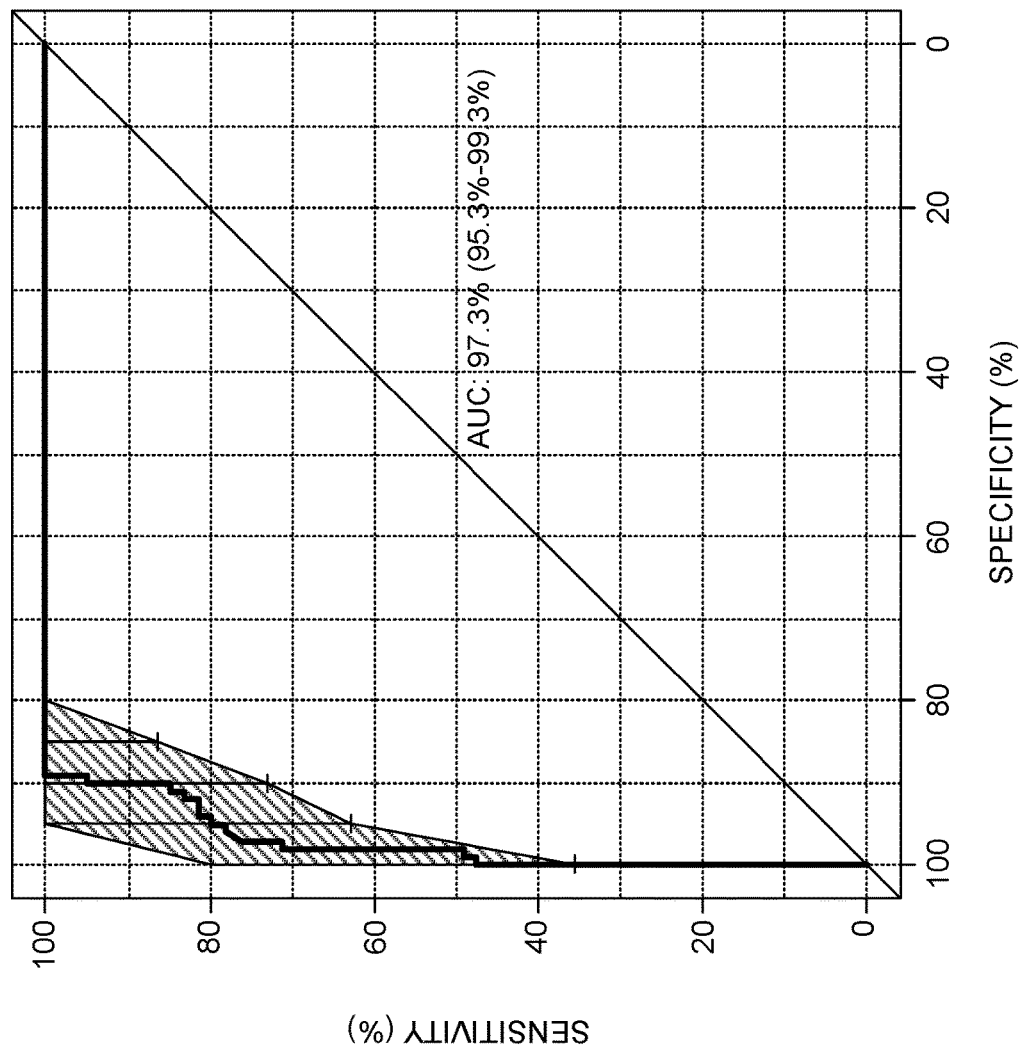
Figure 7:
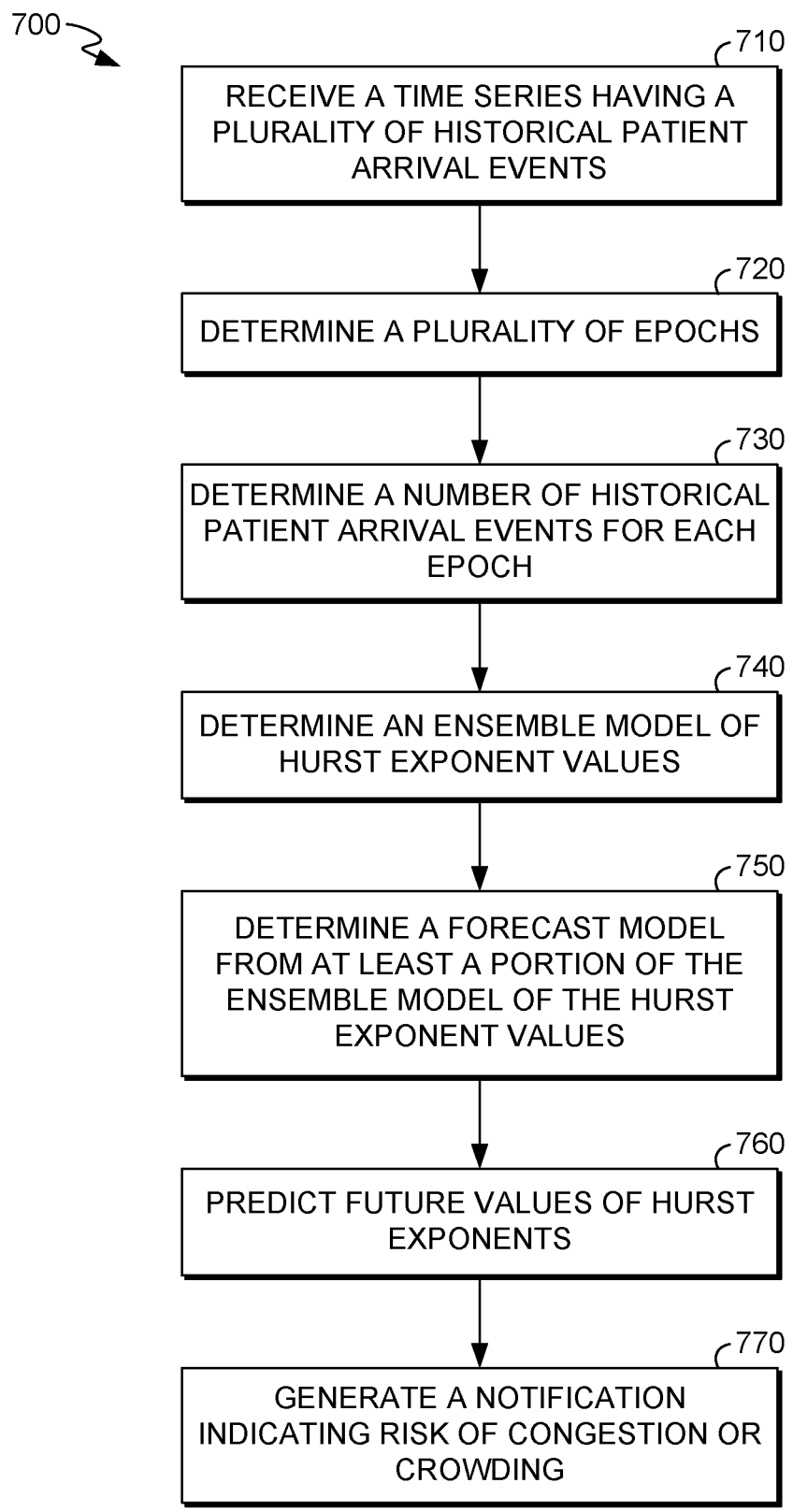

model developed for an example embodiment actually reduced to practice and applied to a time series of 68,914 ED visits;

FIG. 4B depicts an exponentially weighted moving average (EWMA)-smoothing of the ARIMA model developed for an example embodiment actually reduced to practice;

FIG. 5A-5C depict aspects of an example embodiment actually reduced to practice, including a receiver operating characteristic (ROC) curve, descriptive statistics for Hurst exponent distribution, and statistical performance of the example embodiment, respectively;

FIGS. 6A-6B illustratively provide an example embodiment of a computer program routine used by a decision support tool for predicting ED congestion based on determining Hurst self-similarity exponents in the patient-demand time series, in accordance with an embodiment of the present disclosure; and FIG. 7 is a block diagram of an example method suitable for forecasting future patient arrival events and generating a notification indicating risk of congestion or crowding is provided, in accordance with an embodiment of the present disclosure.

DETAILED DESCRIPTION

The subject matter of the present technology is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

The current 'big data' era facilitates a variety of new mathematical and machine-learning based approaches to improving the anticipativeness and responsiveness of services, not only in healthcare but in other industries as well. In addition to assisting in pro-active interventions to prevent occurrences of crowding and on-diversion operations, it is contemplated that embodiments described herein may help service managers to reduce the severity or duration of such occurrences.

Moreover, although the specific examples described herein are generally in the context of healthcare, embodiments of the disclosure may be applied to waiting times or congestion of other services, such as government services (e.g., the post office or department of motor vehicles) or other services. In particular, aligning resources with services utilizers' needs is beneficial to the perceptions that they form regarding the quality and desirability of the provider of those services, as reflected in consumer satisfaction ratings or surveys or other assessments that the services utilizers provide upon completing receiving services from the provider. For resources that have high quality and desirability, incident arrival rates and intensity of demand for services are typically high and fluctuate widely over time, such that queues form and there is significant waiting in order to obtain service. Workload for such high-quality, desirable resources, tends to be high as well, with duty-cycle upwards of 80% for a significant portion of the time. Arrival rates of events associated with service demand tend to fluctuate dramatically, both shift-to-shift and within-shift. New arrivals may wait to receive service enqueued for many hours before service commences during periods of congestion. When congestion is particularly severe, new arrivals may be redirected to alternative providers of service.

As one skilled in the art will appreciate, embodiments of the technology described herein may be embodied as, among other things: a method, system, or set of instructions embodied on one or more computer readable media. Accordingly, the embodiments may take the form of a hardware embodiment, a software embodiment, or an embodiment combining software and hardware. In one embodiment, the technology takes the form of a computer-program product that includes computer-usable instructions embodied on one or more computer readable media.

Computer-readable media can be any available media that can be accessed by a computing device and includes both volatile and nonvolatile media, removable and non-removable media. By way of example, and not limitation, computer-readable media comprises media implemented in any method or technology for storing information, including computer-storage media and communications media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 100. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Accordingly, at a high level, this disclosure describes, among other things, methods and systems, for forecasting ED congestion or determining a likelihood of ED crowding over a future time interval, and for automatically initiating mitigative actions to decrease the risk of future overcrowding. In some embodiments, a decision support tool is provided for resources management to prevent overcrowding and long waiting times. At a high level, embodiments utilize quantitative forecasting of one or more patient-arrival event time series 'self-similarity' measures as a means of predicting near-term future congestion. In particular, in some embodiments, an ensemble-model combining of evidence corresponding to a plurality of estimates of a self-similarity measure, and digital smoothing of serial values produced by the ensemble-model, are utilized to confer robustness of the system and method against false-negative and false-positive errors. In this way, these embodiments of this disclosure further improve upon conventional industry practices and technologies. Additionally, some embodiments utilize an upper control limit threshold in the forecasted self-similarity measure to provide even greater accuracy in predicting imminent congestion, when the threshold is transgressed or satisfied, than is achieved with prior art technologies. The upper control limit threshold, may be empirically-determined, determined based on regulations or hospital policy, and/or set by a hospital administrator. The threshold transgressions may initiate mitigative actions (including generating recommendations) and/or cause electronic notification (e.g., an alarm or warning) or other advisory signals to be emitted to appropriate service managers, so that they can undertake appropriate preventive or corrective or initiate mitigative actions, such as diverting new arrivals to an alternative service, as well as appropriate communications, such as notifying those waiting for service that congestion and delays are anticipated.

Accordingly, as will be further described herein, one embodiment comprises a method for predicting ED congestion or crowding over a future time interval. Information about patient-arrival times are received. The information may be received as a date-time stamped time-series of patient arrival times, and may further include information about demands, such as the particular service(s) or resources the patient requires.

The time series may be pre-processed, in some embodiments, to retain a most amount of time (e.g. T minutes) or number (M1) of events. From the time series or pre-processed time series, arrival events in consecutive epochs are counted. Adjust time series containing identical event counts in all epochs. Next, an ensemble model of Hurst exponent values is determined from the time series. In some embodiments, smoothing is applied to the ensemble-model Hurst exponent time-series.

Using the smoothed Hurst exponent values, a forecast model is determined. Based on the smoothed Hurst exponent values, quantiles of smoothed Hurst exponent n epochs into the future are determined. A comparison may be performed of a forecast future quantile of the smoothed Hurst exponent to an upper control limit (UCL). If the forecast future quantile of the $n^{th}$ future epoch's value of the smoothed Hurst exponent exceeds the upper control limit threshold, then electronic notification, such as an alarm message, may be emitted to responsible managers of the service. Additionally or alternatively, one or more mitigative actions may be invoked, as described herein.

In this way, embodiments described herein overcome deficiencies in the prior art technologies and in particular improve upon the conventional industry practices. In particular, while there have been attempts to provide a technological solution to mitigate ED crowding through decision support systems, these systems have significant drawbacks and cannot provide the reliability and accuracy of the systems and processes proposed in the present disclosure. For example, prior art decision support predictive technologies may take into account finite capacity (number of servers, total number of beds, etc.), but fail to consider the time series or spectral properties from their prediction methods and therefore experience high rates of false-negative prediction errors (i.e., erroneously asserting that no crowding is likely in the near future, when in fact congestion does ensue).

Some prior art decision-support technologies only index the severity of instant congestion that has already materialized and do not forecast future conditions. Other prior art approaches are lagging indicators that are, at best, merely confirmatory of congestion at some time after its onset. While these existing tools and methods may help to provide justification or ethical rationale for diversion decisions that have already been taken; they are completely ineffective for preventive or mitigative interventions to decrease future ED crowding.

The conventional approaches to forecasting impending saturation of available capacity has other deficiencies and limitations as well, including that it: (1) fails to account for nonlinearity and persistent or self-similar patterns in event time series; (2) inadequately accounts for sources of variability in workload, such as patient acuity and turnover; (3) fails to determine the resource sourcing processes and unanticipated/unscheduled changes in capacity; (6) has excessive dependence on values of difficult-to-determine variables and their statistical distributions, such as "boarding time" of patients in ED who are awaiting availability of inpatient beds; (7) has excessive sensitivity to short-term or transient fluctuations in model parameters, causing high rates of false-positive prediction errors; (8) fails to account for heteroskedasticity of variances of arrival and departure processes; and/or (9) lacks the capability to assist in decision-making as to when to return to normal operation and go "off-diversion."

Together, these deficiencies result in a high prevalence of suboptimal services, management decisions, and communications with parties affected by the services, such that delays and congestion occur frequently and customers are frustrated and dissatisfied with the services. In the instance of hospital emergency departments for which false-negative prediction errors occur and the ED is not placed on diversion in a timely manner, there may be a number of patients whose care is delayed such that adverse medical outcomes materialize. In contrast, the embodiments described herein solve these shortcomings in conventional technologies and thus provide significant improvements to decision support technology utilized for predicting ED congestion and managing ED crowding.

Figure 1A:
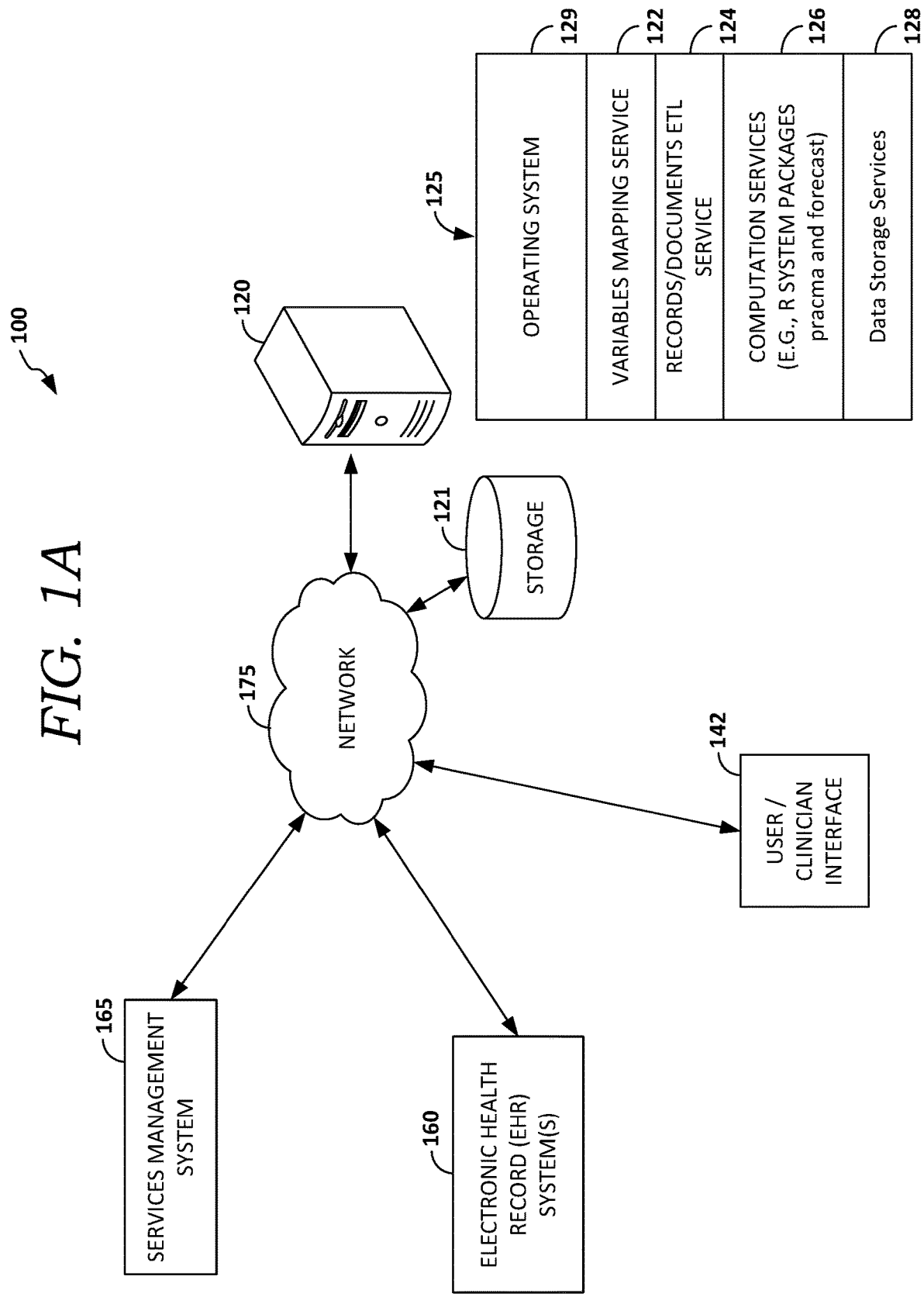

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the technology. Thus for readability, we show and reference items in the singular (while fully contemplating, where applicable, the plural).

As shown in FIG. 1, example operating environment 100 provides an aspect of a computerized system for compiling and/or running aspects of this disclosure, which in some embodiments may include collecting and analyzing unstructured text data from electronic health record(s), which may include claims data, to assess the texts as to topical or concept-oriented expressions they contain that are statistically similar to those associated with various clinical conditions or diagnoses; to identify which condition- or diagnosis-oriented clusters the present texts most closely resemble, if any; and to notify the responsible clinicians of those determinations, suggesting consideration of those conditions or diagnoses as part of the constellation of differential diagnoses pertinent to the management of the current patient.

Operating environment 100 is one example of a suitable environment and system architecture for implementing an embodiment of the disclosure. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Environment 100 includes a services management system 165 and one or more electronic health record (EHR) system(s) 160 communicatively coupled to network 175, which is communicatively coupled to computer system 120. In some embodiments, components of environment 100 that are shown as distinct components may be embodied as part of or within other components of environment 100. For example, EHR system 160 may comprise one or a plurality of hospital EHR systems, health information exchange EHR systems, clinical genetics/genomics systems, ambulatory clinic EHR systems, psychiatry/neurology EHR systems, insurance, collections or claims records systems; and may be implemented in computer system 120. In an embodiment, EHR system(s) 160 includes historical data for patient addition treatment, relapse information, other health services, claims data, apportionment data, and/or related health services financial data.

In some embodiments, sequence itemset mining is performed using data about a population of patients derived from patient EHR information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of services management system 165 may comprise one or more management computer application(s) or computing system (which may be distributed in a hospital system, in some embodiments) and used for managing services, such as ED services. Some embodiments of services management system 165 may include functionality for managing service-related resources (e.g., staffing, hospital beds, equipment, etc.) such as resource scheduling, re-routing or diversion of patients (or users of the services), various real-time or predictive services (such as ED congestion prediction), and/or warning systems, which may be utilized for emitting an alert indicating possible future ED crowding.

160 Embodiments of EHR system(s) 160 may comprise one or more data stores of health records, which may be stored on storage 121, and may further include one or more computers or servers that facilitate the storing and retrieval of the health records. In some embodiments, EHR system(s) 160 may be implemented as a cloud-based platform or may be distributed across multiple physical locations. EHR system(s) 160 may further include record systems, which store real-time or near real-time patient (or user) information, such as wearable, bedside, or in-home patient monitors or sensors, for example. Although FIG. 1A depicts an exemplary EHR system(s) 160, it is contemplated that an embodiment relies on services management system 165 or user/clinician interface 142 for accessing, storing and/or retrieving patient record information.

Example operating environment 100 further includes a clinician/user interface 142 communicatively coupled through network 175 to services management system 165 and EHR system(s) 160. Although environment 100 depicts an indirect communicative coupling between application 142 and other components of environment 100, through network 175, it is contemplated that an embodiment of application 142 is communicatively coupled to these components directly. An embodiment of interface 142 comprises a user interface and software application or set of applications residing on a client computing device (or distributed in the cloud and on a client computing device) such as a personal computer, laptop, smartphone, tablet, or mobile computing device. In an embodiment, the application includes the PowerChart® software manufactured by Cerner Corporation. In an embodiment, interface 142 includes a Web-based application (which may take the form of an applet or app) or set of applications usable to manage user services provided by an embodiment of the disclosure. Interface 142 may be used to provide or manage user services provided by an embodiment of the disclosure; for instance interface 142 may be used by a clinician or ED manager to predict a risk of future congestion to initiate mitigating actions and/or review recommendations.

Additionally, in some embodiments, interface 142 facilitates accessing and receiving information from a health record, or health care provider about a specific patient, set of patients, or provider clinicians, according to the embodiments presented herein. Embodiments of interface 142 also may facilitate accessing and receiving information from a user or health care provider about a specific patient or population of patients including patient history; health care resource data; variables measurements, timeseries, and predictions (including plotting or displaying the determined outcome and/or issuing an alert) described herein; or other health-related information, and facilitates the display of results, recommendations, or orders, for example. In an embodiment, interface 142 also facilitates receiving orders for the patient/target user from the clinician/caregiver/manager, based on the results of monitoring and/or predictions. In an embodiment, interface 142 may present (or provide an indication of) an alarm or communication regarding risk of future ED congestion (or no likelihood of congestion). Interface 142 may also be used for providing diagnostic services or evaluation of the performance of various embodiments.

Example operating environment 100 further includes computer system 120, which may take the form of a server, which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, a portion of computing system 120 may be embodied on services management system 165 and/or interface 142. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as a local or distributed stack in the cloud, on one or more personal computers or servers such as system 120, and/or computing device(s) running interface 142 and/or services management system 165. In some embodiments, interface 142 and/or services management system 165 operate in conjunction with software stack 125.

In embodiments, model variables indexing (or mapping) service 122 and records/documents ETL service 124 provide services that facilitate retrieving frequent item sets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, these services may invoke computation services 126.

Computation services 126 perform statistical software operations, and include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services, and R-system modules or packages including, in an embodiment, pracma package, which may be utilized for carrying out functions including numerical analysis and linear algebra, numerical optimization and differential equations; and the forecast package, which may be utilized for carrying out forecasting functions for time series and linear models; or other similar services.

In some embodiments, computational services include natural language processing services (not shown) such as Discern nCode™ developed by Cerner Corporation, or similar services. In an embodiment, computation services 126 include the services or routines, which may be embodied as one or more software agents or computer program routines such as the example embodiments of computer program routines illustratively provided in FIGS. 6A-6B. In some embodiments, computation services 126 may be utilized by system manager services 165. Some embodiments of computation services 126 may use data storage services 128. Data storage services 128. Include services for facilitating receiving (or determining) one or more time series, as described herein, which may include time-series derived models (e.g. ARIMA models) as described in connection to FIG. 2.

Some embodiments of stack 125 may further use Apache Hadoop and Hbase framework (not shown), or similar frameworks operable for providing a distributed file system, and which in some embodiments facilitate provide access to cloud-based services such as those provided by Cerner Healthe Intent®. Further, some embodiments of stack 125 may use predictive models services or routines (not shown) for forecasting future crowding, which in one embodiment may be developed and implemented according to the method described in connection to FIG. 2. Additionally, some embodiments of stack 125 may further comprise one or more services stream processing service(s) (not shown). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the technology also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with treatment/relapse logging system 160. Further, although depicted as a single storage data store, data store 121 may comprise one or more data stores, or may be in the cloud.

Turning briefly now to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north Bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
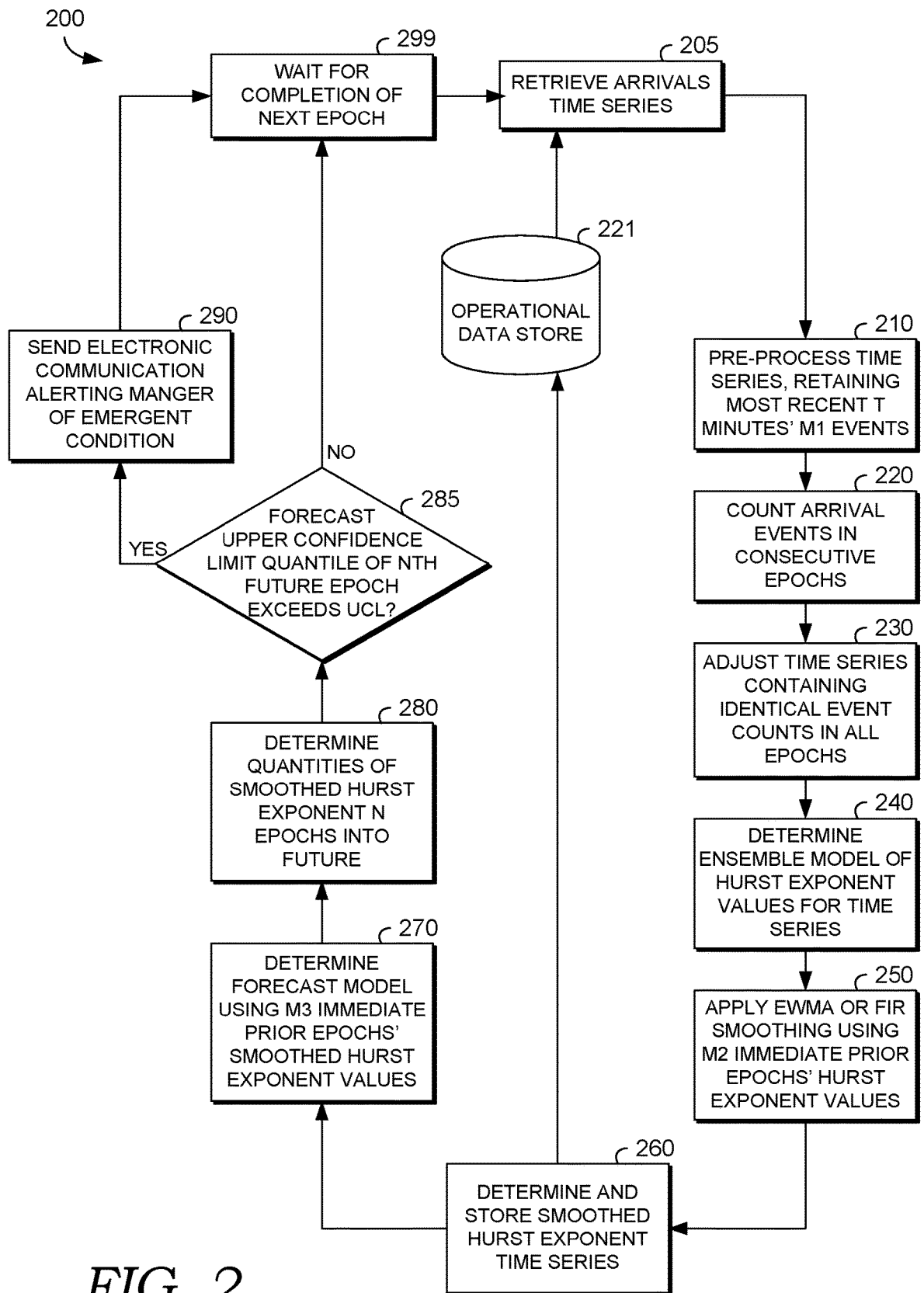
FIG. 2 depicts a flow diagrams of a method for predicting ED congestion or crowding over a future time interval by determining Hurst parameters from a patient-arrivals time series, in accordance with an embodiment of the present disclosure.

Turning now to FIG. 2, a method 200 is provided for predicting ED congestion or crowding over a future time interval. With continuing reference to FIG. 2 and method 200, statistical analyses of measurements of computer network and telecomm traffic from a wide variety of sources show that correlations persist in such sources over fairly long time scales. Our investigation into health care services show that a time series of health care services' arrival and departure times exhibit 'self-similar' properties of this type as well. This has called into question the use of traditional traffic models for the performance analysis of communication networks and has sparked considerable research on the use of long range-dependent traffic models for such performance analysis.

In resource capacity analysis, an observation is presented that the tail behavior of queues with long-range-dependent 'self-similar' inputs decays much slower than exponentially. This may be represented by a sub-exponential Weibull law (for example, like $\exp(-c*x^\gamma)$ for some $0<\gamma<1$) and in other instances it decays algebraically according to a Power law (like $c*x^{-\gamma}$ for some $\gamma>0$). The presence of a qualitative difference in queueing behavior with the traffic measured as compared to that predicted enables one to perform load-balancing or allocation of newly-arriving demand to selected servers that do not have such pronounced long-range-dependent self-similar properties.

The most tractable traffic models result when inter-arrival times and workload sequences are independent random variables and independent of each other. A self-similar-based model implies that the traffic variations are statistically similar over many, theoretically infinite ranges of timescales. As a result, one observes temporal dependence in the traffic structures over large time intervals. Our investigation and results for time series of health care arrival events and service times show temporal dependence in the inter-arrival intervals and epochal event counts of this type.

Traffic bursts are structures characterized by a successive occurrence of several short inter-arrival times followed by a relatively long inter-arrival time. Correspondingly, traffic bursts are characterized by consecutive epochs with larger event counts followed by subsequent epochs having smaller event counts.

The presence of correlations in the arrival rate for lags greater than zero cause the arrival process to be over-dispersed relative to Poisson processes with constant arrival rate. The degree of dispersion is proportional to the decay rate. Increased traffic variability has an impact on the problem of resource allocation and engineering. In this connection, when the Hurst exponent (H) takes on values in the range 0.5-1.0, it indicates a time series that possesses long-term positive autocorrelation, or is 'self-similar' over long timescales. Values of H exceeding 0.8 generally denote a process that is congested or nearing saturation of the available service capacity. By contrast, H in the range 0.0-0.5 indicates a time series with persistent switching between high and low values in adjacent pairs, meaning that a single high value will probably be followed by a low value and that the value after that will tend to be high, with this tendency to switch between high and low values lasting a long time into the future. The special case of H=0.5 can indicate a random, completely uncorrelated time series, but in fact it is the value applicable to series for which the autocorrelations at small time lags can be positive or negative but where the absolute values of autocorrelations decay exponentially quickly to zero (a stable, mean-reverting process).

Accordingly, method 200 begins at step 205, wherein information about patient-arrival times are received. The information may be received as a date-time stamped time-series of patient arrival times, and may further include information about demands, such as the particular service(s)

or resources the patient requires. In some embodiments, patient arrivals information is formatted into a time-series. The information may comprise recent historical arrivals event time series data (e.g., previous 120 minutes' arrivals) for a service process of interest, and may be received from an operational data store 221, which may be embodied as storage 121 or FIG. 1A. The information may be derived from a services management system 165 or EHR 160, as described in connection to FIG. 1A. In some embodiments, data storage services 128 are utilized to facilitate receiving (or determining) the time series.

One example time series of patient arrivals to an ED is illustratively provided in FIG. 3. Turning briefly to FIG. 3, a portion of an example of an arrival time series 300 includes information about a series of patient visits by patients to an ED. The information in this example arrival time series 300 includes, among other information, a date-time stamp of the visit time ("dt_tm"), a visit ID, and information about the emergency type ("enc_typ") or service (e.g. resources) needed by the particular patient.

Returning to FIG. 2 and method 200, at step 210, the time series may be pre-processed, in some embodiments, to retain a most amount of time (e.g. T minutes) or number (M1) of events. For example, in one embodiment, the previous 120 minutes' arrivals are used, or in another embodiment, the previous 120 minutes' arrivals for a particular service process of interest (e.g., "emergency," inpatient, OBS, (observation services), etc.).

At step 220, from the time series or pre-processed time series, arrival events in consecutive epochs are counted. Embodiments of step 220 count arrival events accruing in consecutive time periods or epochs (e.g., epochs of 5-min length). At step 230, adjust time series containing identical event counts in all epochs. Embodiments of step 230 adjust the counts time series containing identical counts (e.g., by incrementing count in first epoch by 1).

At step 240, an ensemble model of Hurst exponent values is determined from the time series. Embodiments of step 240 first determine Hurst exponent of event-count-by-epoch time series. In particular, a plurality of estimation methods may be utilized to determine the Hurst exponents, such as R/S, Higuchi, Wavelet, multi-taper spectral method, fractional exponent, autocovariance function ACVF, corrected empirical method, or similar approaches. Then using the Hurst exponents, embodiments of step 240 construct an ensemble model (a first model constructed by method 200) from the plurality of estimated Hurst exponent values. In one embodiment, the ensemble is constructed from averaging the values.

At step 250, in some embodiments, smoothing is applied to the ensemble-model Hurst exponent time-series. For example, exponential weighted moving average (EWMA) smoothing or finite-impulse response (FIR) low-pass filtering may be applied. In some embodiments of step 250, the smoothing may be applied using a number (M2) of immediate prior epoch's Hurst exponent values. At step 260, the smoothed Hurst exponent time series may be stored in storage 121, where it may be available for future instances of method 200.

At step 270, using the smoothed Hurst exponent values, a forecast model is determined. In some embodiments, the forecast model is determined using a number (M3) of immediate prior epochs' smoothed Hurst exponent values. In particular, embodiments of step 270 construct a forecast model (a second model constructed by method 200) from smoothed ensemble-model Hurst exponent time-series. In an embodiment this second model comprises an autoregressive integrated moving average (ARIMA) model.

Based on the smoothed Hurst exponent values, at step 280, quantiles of smoothed Hurst exponent n epochs into the future are determined. Embodiments of step 280 determine a forecast quantile value or, alternatively, quantiles for a plurality of future values of the smoothed Hurst exponent of the event arrival process. For example, in one embodiment, the quantiles may be determined for three five-minute epochs into the future (or 15 minutes). An example of the 75th-percentile Hurst exponent distributions for a 15-minute future interval determined from an example ARIMA model from step 270 is illustratively provided in FIG. 4A. These Hurst exponent distributions correspond to an embodiment actually reduced to practice and applied to a time series of 68,914 ED visits (patient arrivals). FIG. 4B depicts an example of the ARIMA model time series wherein exponentially weighted moving average (EWMA)-smoothing has been applied. It can be seen in FIG. 4B that in two instances where high demand (i.e. congestion) was forecasted, ED diversion was implemented (as shown by the ED diversion intervals).

At step 285, a comparison is performed of a forecast future quantile of the smoothed Hurst exponent to an upper control limit (UCL). In particular, embodiments of step 285 compare the upper confidence limit of the quantile for the $n^{th}$ future epoch (e.g., 3 epochs into the future). If the forecast upper confidence limit quantile of $n^{th}$ future epoch exceeds the upper control limit, then a risk of future congestion is likely or sufficiently probable, and method 200 proceeds to step 290, where an electronic notification is issued and/or mitigative action is invoked. Otherwise, a risk of future congestion is unlikely and method 200 proceeds to step 299.

At step 290, if the forecast future quantile of the $n^{th}$ future epoch's value of the smoothed Hurst exponent exceeds the upper control limit threshold, then electronic notification, such as an alarm message, may be emitted to responsible managers of the service. Additionally or alternatively, one or more mitigative actions may be invoked. The upper control limit threshold may be empirically-determined, determined based on regulations or hospital policy, and/or set by a hospital administrator. The mitigative actions may comprise automatically diverting new arrivals to an alternative service or ED location, automatically scheduling additional resources, staffing, or triage services, as well as appropriate communications, such as notifying those waiting for service that congestion and delays are anticipated. In some embodiments, the mitigative actions may include generating recommendations and/or cause electronic notification (e.g., an alarm or warning) or other advisory signals to be emitted to appropriate service managers, so that they can undertake appropriate preventive or corrective or initiate mitigative actions, such as diverting new arrivals to an alternative service.

At step 299, method 200 waits for the completion of the next epoch of time before repeating. Some embodiments of the steps of method 200 may utilize computation services 126 including the R-system packages pracma and forecast. Additionally, some embodiments of these steps may be implemented using the example computer program routine depicted in FIGS. 6A and 6B. It is further contemplated that some embodiments of method 200 (which may include an implementation such as the example computer program routine shown in FIGS. 6A-6B) may operate within a decision support tool and may be utilized in an ongoing or continuous manner, periodically, or as needed. For instances, some embodiments may operate only during times where peak demand is more likely to occur. Additionally, it is contemplated that the epoch lengths of method 200 may be varied based on when the method is utilized, the number of arrivals, and/or the particular services (or resources) the patients are seeking or the resources available.

Turning now to FIG. 7, an example method 700 suitable for forecasting future patient arrival events and generating a notification indicating risk of congestion or crowding is provided. At block 710, a time series having a plurality of historical patient arrival events is received. In some cases, the plurality of historical patient events may be received from an electronic medical record system. In some cases, each historical patient arrival event of the plurality of historical patient arrival events has a date-time stamp associated with the arrival event. At block 720, a plurality of epochs is determined from the time series. In some cases, each epoch comprises a fixed length of time. At block 730, a number of historical patient arrival events for each epoch of the plurality of epochs is determined. In some cases, the time series may be pre-processed to retain one or more historical patient arrival events in a most recent epoch of the time series. In some cases, the time series may be adjusted so that each epoch of the plurality of epochs comprises a same number of historical patient arrival events.

At block 740, an ensemble model of Hurst exponent values is determined. In some cases, the ensemble model of Hurst exponent values is determined based on at least a portion of the number of historical patient arrival events for each epoch of the plurality of epochs. In some cases, the Hurst exponent values of the ensemble may be determined utilizing an R/S method, a Higuchi method, a wavelet analysis, a multi-taper spectral method, a fractional exponent method, an autocovariance function, or a corrected empirical method. In some cases, the ensemble model of Hurst exponent values is further determined by averaging the Hurst exponent values determined using the R/S method, the Higuchi method, the wavelet analysis, the multi-taper spectral method, the fractional exponent method, the autocovariance function, or the corrected empirical method. In some cases, the ensemble model of Hurst exponent values may be smoothed by utilizing an exponential weighted moving average (EWMA) method or a finite-impulse response (FIR) low-pass filtering method.

At block 750, a forecast model is determined from at least a portion of the ensemble model of the Hurst exponent values. In some cases, the forecast model comprises an autoregressive (AR) method, an autoregressive moving average (ARMA) method, or an autoregressive integrated moving average (ARIMA) method. In some cases, a second forecast model is determined. In some cases, the second forecast model comprises an autoregressive integrated moving average (ARIMA) model. In some cases, the future values of Hurst exponents are further predicted based on the second forecast model. At block 760, future values of Hurst exponents are predicted. In some cases, the future values of Hurst exponents are predicted utilizing the forecast and/or the second forecast models. In some cases, the future values of Hurst exponents forecast future patient arrival events.

At block 770, a notification indicating risk of congestion or crowding is generated. In some cases, the notification indicates risk of congestion or crowding over a future time interval. In some cases, the future time interval comprises one or more future epochs. In some cases, the notification is generated based on comparing the future values of Hurst exponents to a predetermined upper control limit. In some cases, the notification is generated based on the future values of Hurst exponents exceeding the predetermined upper control limit. In some cases, a mitigative action may be performed based on the future values of Hurst exponents. In some cases, the mitigative action may comprise causing a diversion of new patient arrival events, notifying individuals awaiting services of anticipated delays, automatically scheduling additional staffing resources, or initiating triage services.

Example Reduction to Practice

With continuing reference to the drawings, an example embodiment reduced to practice is now described. Reduction to practice was accomplished using a computer running the Linux operating system (operating system 129), the open-source statistical software package R (software services 126), and the R package pracma.

For the example reduction to practice, an illustrative series was retrieved, consisting of 68,914 de-identified, privacy-protected, secondary-use-permitted HIPAA-compliant ED arrival records for 2 large institutions' emergency departments (1 Jan. 2016 to 30 Jun. 2016). This time period contained 60 intervals when an ED had exhibited the composite endpoint consisting of 'on-diversion' status or mean service time exceeding the 6-month 75th percentile service time for the ED.

Initial results for hospital ED data indicate that a time series of at least 2 hours' arrivals data (24 five-minute epochs) is desired for numerically reliable forecasting of the demand and response processes in hospital-based emergency medicine services. An ensemble model of Hurst exponent values was determined utilizing an embodiment based on method 200, described in connection to FIG. 2, and the example computer program routine illustratively provided in FIGS. 6A-6B. In this example embodiment, the ensemble model was determined as the mean of the corrected empirical method for determining the Hurst exponent and the R/S method. The arrivals regime ensemble-model Hurst exponent values in this example data set ranged from 0.000 to 1.000. The ensemble-model Hurst exponent values were smoothed by exponentially-weighted moving average (EWMA) with a lambda value of 0.2 and a smoothing window of 12 epochs. As each successive epoch was concluded, an autoregressive integrated moving average (ARIMA) forecast was determined from the prior 24 epochs' EWMA-smoothed ensemble-model Hurst exponent H values. To provide advance notice of impending congestion and deterioration of service times, 15-min-ahead forecasting was determined using the ARIMA model, and the 75th percentile of the forecast H value was determined. A threshold of 0.80 was established as an upper control limit (UCL) for purposes of predicting near-term future congestion or ED-diversion status. When the $75^{th}$ percentile of the 15-min-ahead forecast H value exceeded the UCL, a warning signal was generated and electronically communicated to the ED management personnel, indicating the imminent likelihood of an overcrowded condition in the service. The departures time series Hurst exponent values did not exhibit a similar relationship to congestion or diversion status. Descriptive statistics are shown in Tables 1 and 2. Arrivals time series 15-min-ahead UCL transgressions Receiver Operating Characteristic (ROC) area-under-the-curve was 97.3% (as shown in FIG. 5A), indicating excellent accuracy and calibration of the forecasts to actual subsequent congestion or diversion of the EDs. In the reduction-to-practice example, similar results were obtained with forecasting horizons up to 120-min-ahead, albeit with lower sensitivity and specificity (as shown in FIG. 5C). FIG. 5B shows additional descriptive statistics for the Hurst exponent distributions of the example embodiment actually reduced to practice.

Many different arrangements of the various components depicted, as well as components not shown, are possible without departing from the spirit and scope of the present technology. Embodiments of the present technology have been described with the intent to be illustrative rather than restrictive. Alternative embodiments will become apparent to those skilled in the art that do not depart from its scope. A skilled artisan may develop alternative means of implementing the improvements described herein without departing from the scope of the technology. For example, some embodiments may include the following:

Embodiment 1: A method for predicting congestion or crowding of services over a future time interval comprising: storing a time series of date-timestamped arrival events in machine-readable media; periodically retrieving a recent segment of said time series from the machine-readable media for analysis; optionally appending a newly incoming instance of the event type to said time series; pre-processing the resulting time series so as to retain just those events that accrued within a most recent specific time interval; dividing the time dimension into intervals or 'epochs' of a fixed length; tallying the number of events accruing within each such epoch; calculating at each epoch a self-similarity measure for moving-window successive segments of the time series by a plurality of methods; assembling the plurality of resulting values for the self-similarity measure in each epoch into an ensemble model estimate of the self-similarity measure; smoothing the serial values of the ensemble-model self-similarity measure estimates; calculating a quantitative forecasting model from a subset of the most recent values of said smoothed ensemble-model self-similarity measure estimates of the self-similarity measure; by using said forecasting model, forecasting future one or more quantile values of the smoothed ensemble-model estimates of the self-similarity measure; comparing one or more of said future values to an upper control limit threshold; emitting to responsible service managers an electronic warning signal or communication if the upper control limit is exceeded, alerting the managers to the predicted near-term threshold transgression and congestion-related service time exceedance; storing the smoothed ensemble-model estimates of the self-similarity measure and the forecast value and associated forecast quantile-UCL comparison in machine-readable media.

Embodiment 2: The method of embodiment 1, wherein the events denoting newly arriving entities requiring services are date-timestamped and tallied into a plurality of consecutive short time-period epochs where the epoch length is (a) short compared to the time intervals over which service time and queueing time deteriorate or improve and (b) long enough so that a majority of epochs will contain at least one arrival event. In the case of busy emergency medicine services, epoch length is preferably between 3 minutes and 15 minutes, and more preferably between 5 minutes and 10 minutes.

Embodiment 3: The method of any of embodiments 1-2, wherein the quantitative forecast modeling may include autoregressive (AR), autoregressive moving average (ARMA), autoregressive integrated moving average (ARIMA), or other forecasting methods applied to historical time series for the services venue in which said forecasts are to be produced.

Embodiment 4: The method of any of embodiments 1-3, wherein the self-similarity property of said time series is the Hurst exponent.

Embodiment 5: The method of any of embodiments 1-4, wherein the Hurst exponent of said time series is calculated by at least two of a plurality of methods, such as R/S, Higuchi, Wavelet, multi-taper spectral method, fractional exponent, autocovariance function ACVF, or the corrected empirical method.

Embodiment 6: The method of any of embodiments 1-5, wherein smoothing of the time series of values of the self-similarity measure is an exponentially-weighted moving average or finite impulse response low-pass filter to smooth.

Embodiment 7: The method of any of embodiments 1-6, wherein the smoothing is applied to a time series segment between 4 and 15 epochs in length, preferably between 8 and 12 epochs in length.

Embodiment 8: The method of any of embodiments 1-7, wherein the adjustment of arrival-event count time series containing identical counts in all of the epochs in the selected time segment consists in incrementing at least one of the epoch counts by a small value, such as incrementing the count in said epoch or epochs by 1.

Embodiment 9: The method of any of embodiments 1-8, wherein each consecutive determination of the self-similarity metric is stored in computer readable media.

Embodiment 10: The method of any of embodiments 1-9, wherein the retrieved recent segment of arrival-event time series comprises arrival events within a period of time adjoining the current time and extending backward across a span of time that is sufficiently long as to be adequately representative.

Embodiment 11: The method of any of embodiments 1-10, wherein the methods for estimation of the Hurst exponent includes de-meaning or centering of the epoch count time series, so that automatic adaptation to services of different sizes and potentially varying sizes and varying staffing are automatically accommodated.

Embodiment 12: The method of any of embodiments 1-11, wherein serial forecasts are either prepared on an event-driven basis at each time that a new arrival occurs or, alternatively, are prepared on a periodic, batch basis (for example, by map-reduce processing, for example, at the end of each elapsing epoch interval).

Embodiment 13: The method of any of embodiments 1-12, wherein the forecast model is determined from the immediate prior time series segment between 20 and 100 epochs in length, preferably between 24 and 48 epochs in length.

Embodiment 14: The method of any of embodiments 1-13, wherein the forecast model is applied to forecast values of the smoothed self-similarity measure that are likely to materialize in a plurality of succeeding future epochs comprising a time segment between 2 and 50 epochs in length, preferably between 3 and 10 epochs in length.

Embodiment 15: The method of any of embodiments 1-14, wherein the forecast values include one or more selected statistical quantiles of the predicted probability distribution of future values of the smoothed self-similarity measure.

Embodiment 16: The method of any of embodiments 1-15, wherein an upper control limit (UCL) of the Hurst exponent is selected to be between 0.70 and 0.95, preferably between 0.80 and 0.85.

Embodiment 17: The method of any of embodiments 1-16, wherein the selected quantile is between 70 and 99.9, preferably between 75 and 90.

Embodiment 18: The method of any of embodiments 1-17, wherein comparison is made between the selected future-epoch quantile value and the selected UCL and wherein an advisory message or alarm indicia is set or emitted when the future-epoch quantile value exceeds the UCL.

Embodiment 19: The method of any of embodiments 1-18, wherein comparison is made between the selected future-epoch quantile value and the selected UCL and wherein an advisory message or alarm indicia is cleared or retracted when the future-epoch quantile value is less than the UCL.

Embodiment 20: The method of any of embodiments 1-19, wherein the electronic communication of the advisory message or alarm indicia is by means of an online system, such as an electronic health record system, SMS text messaging, pager, Hospital Operations Dashboard (HOD) online display, or similar means.

It will be understood that certain features and subcombinations are of utility and may be employed without reference to other features and subcombinations and are contemplated within the scope of the claims. Not all steps listed in the various figures need be carried out in the specific order described. Accordingly, the scope of the technology is intended to be limited only by the following claims.

What is claimed is:

1. A computer-implemented method for predicting congestion or crowding of services over a future time interval, comprising utilizing a processor for executing computer-readable media having instructions stored thereon that cause the processor to:
   receive a time series having a plurality of historical patient arrival events, each historical patient arrival event of the plurality of historical patient arrival events having a date-time stamp;
   from the time series, determine a plurality of epochs of a fixed length of time;
   determine a number of historical patient arrival events for each epoch of the plurality of epochs;
   determine an ensemble model of Hurst exponent values based on at least a portion of the number of historical patient arrival events for each epoch of the plurality of epochs;
   determine a forecast model from at least a portion of the ensemble model of the Hurst exponent values;
   utilize the forecast model, predicting future values of Hurst exponents to forecast future patient arrival events;
   based on the future values of Hurst exponents, generate a notification indicating risk of congestion or crowding over the future time interval, wherein the future time interval comprises one or more future epochs; and
   automatically perform, by a computerized decision-support tool, a mitigative action based on the future values of Hurst exponents, wherein the mitigative action comprises causing a diversion of new patient arrival events, notifying individuals awaiting services of anticipated delays, or initiating triage services.

2. The method of claim 1, further comprising pre-processing the time series to retain one or more historical patient arrival events in a most recent epoch of the time series.

3. The method of claim 1, further comprising adjusting the time series so that each epoch of the plurality of epochs comprises a same number of historical patient arrival events.

4. The method of claim 1, wherein the Hurst exponent values are determined utilizing an R/S method, a Higuchi method, a wavelet analysis, a multi-taper spectral method, a fractional exponent method, an autocovariance function, or a corrected empirical method.

5. The method of claim 4, wherein the ensemble model of Hurst exponent values is further determined by averaging the Hurst exponent values determined from the R/S method, the Higuchi method, the wavelet analysis, the multi-taper spectral method, the fractional exponent method, the autocovariance function, or the corrected empirical method.

6. The method of claim 1, further comprising smoothing the ensemble model of Hurst exponent values by utilizing an exponential weighted moving average (EWMA) method or a finite-impulse response (FIR) low-pass filtering method.

7. The method of claim 1, further comprising determining a second forecast model comprising an autoregressive integrated moving average (ARIMA) model, wherein the future values of Hurst exponents are further predicted based on the second forecast model.

8. The method of claim 1, wherein generating the notification is based on comparing the future values of Hurst exponents to a predetermined upper control limit, and wherein the notification is generated based on the future values of Hurst exponents exceeding the predetermined upper control limit.

9. Computer-readable media having computer-executable instructions stored thereon that, when executed by a processor, cause the processor perform operations for predicting congestion or crowding of services over a future time interval, the operations comprising:
   receiving a time series having a plurality of historical patient arrival events, each historical patient arrival event of the plurality of historical patient arrival events having a date-time stamp;
   from the time series, determining a plurality of epochs of a fixed length of time;
   determining a number of historical patient arrival events for each epoch of the plurality of epochs;
   determining an ensemble model of Hurst exponent values based on at least a portion of the number of historical patient arrival events for each epoch of the plurality of epochs;
   determining a forecast model from at least a portion of the ensemble model of the Hurst exponent values;
   utilizing the forecast model, predicting future values of Hurst exponents to forecast future patient arrival events;
   based on the future values of Hurst exponents, generating a notification indicating risk of congestion or crowding over the future time interval, wherein the future time interval comprises one or more future epochs; and
   automatically performing, by a computerized decision-support tool, a mitigative action based on the future values of Hurst exponents, wherein the mitigative action comprises causing a diversion of new patient arrival events, notifying individuals awaiting services of anticipated delays, or initiating triage services.

10. The media of claim 9, further comprising:
    pre-processing the time series to retain one or more historical patient arrival events in a most recent epoch of the time series; and adjusting the time series so that each epoch of the plurality of epochs comprises a same number of historical patient arrival events.

11. The media of claim 9, wherein the forecast model comprises an autoregressive (AR) method, an autoregressive moving average (ARMA) method or an autoregressive integrated moving average (ARIMA) method.

12. The media of claim 9, wherein the Hurst exponent values are determined utilizing an R/S method, a Higuchi method, a wavelet analysis, a multi-taper spectral method, a fractional exponent method, an autocovariance function, or a corrected empirical method.

13. The media of claim 12, wherein the ensemble model of Hurst exponent values is further determined by averaging the Hurst exponent values determined from the R/S method, the Higuchi method, the wavelet analysis, the multi-taper spectral method, the fractional exponent method, the autocovariance function, or the corrected empirical method.

14. The media of claim 9, further comprising smoothing the ensemble model of Hurst exponent values by utilizing an exponential weighted moving average (EWMA) method or a finite-impulse response (FIR) low-pass filtering method.

15. The media of claim 9, further comprising determining a second forecast model comprising an autoregressive integrated moving average (ARIMA) model, wherein the future values of Hurst exponents are further predicted based on the second forecast model.

16. The media of claim 9, wherein generating the notification is based on comparing the future values of Hurst exponents to a predetermined upper control limit, and wherein the notification is generated based on the future values of Hurst exponents exceeding the predetermined upper control limit.

17. A computerized decision-support tool for predicting congestion or crowding of services over a future time interval, the method comprising, the decision support tool comprising:
   a user interface configured to provide decision support information; and
   a processor for executing computer-readable media having instructions stored thereon that cause the processor to:
      receive a time series having a plurality of historical patient arrival events, each historical patient arrival event of the plurality of historical patient arrival events having a date-time stamp;
      from the time series, determine a plurality of epochs of a fixed length of time;
      determine a number of historical patient arrival events for each epoch of the plurality of epochs;
      determine an ensemble model of Hurst exponent values based on at least a portion of the number of historical patient arrival events for each epoch of the plurality of epochs;
      determine a forecast model from at least a portion of the ensemble model of the Hurst exponent values;
      utilizing the forecast model, predict future values of Hurst exponents to forecast future patient arrival events;
      based on the future values of Hurst exponents, generate a notification for display on the user interface, the notification indicating risk of congestion or crowding over the future time interval, wherein the future time interval comprises one or more future epochs; and
      automatically perform, by the computerized decision-support tool, a mitigative action based on the future values of Hurst exponents, wherein the mitigative action comprises causing a diversion of new patient arrival events, notifying individuals awaiting services of anticipated delays, or initiating triage services.

18. The computerized decision-support tool of claim 17, wherein the forecast model comprises an autoregressive (AR) method, an autoregressive moving average (ARMA) method, or an autoregressive integrated moving average (ARIMA) method.

* * * * *